United States Patent [19]

Bell et al.

[11] Patent Number: 6,087,306
[45] Date of Patent: Jul. 11, 2000

[54] GRANULE COMPOSITION

[75] Inventors: Gordon Alastair Bell; Susan Marie Critchley, both of Yalding Nr Maidstone, United Kingdom

[73] Assignee: Zeneca Limited, United Kingdom

[21] Appl. No.: 09/051,821

[22] PCT Filed: Oct. 18, 1996

[86] PCT No.: PCT/GB96/02568

§ 371 Date: Apr. 22, 1998

§ 102(e) Date: Apr. 22, 1998

[87] PCT Pub. No.: WO97/15186

PCT Pub. Date: May 1, 1997

[30] Foreign Application Priority Data

Oct. 24, 1995 [GB] United Kingdom ............... 9521707

[51] Int. Cl.$^7$ ........................ A01N 25/12; A01N 25/14
[52] U.S. Cl. ............................... 504/367; 514/777
[58] Field of Search .................... 504/116, 367; 514/777

[56] References Cited

U.S. PATENT DOCUMENTS

| | | | |
|---|---|---|---|
| 4,874,423 | 10/1989 | Colegrove et al. | 71/95 |
| 5,248,709 | 9/1993 | Brehm | 523/221 |
| 5,294,594 | 3/1994 | Kimler et al. | 504/116 |
| 5,332,524 | 7/1994 | Kaylor | 252/4 |
| 5,393,731 | 2/1995 | Kimler et al. | 504/139 |

FOREIGN PATENT DOCUMENTS

| | | |
|---|---|---|
| 0089588 | 3/1983 | European Pat. Off. |
| 0112438 | 9/1983 | European Pat. Off. |
| 0415688 | 8/1989 | European Pat. Off. |
| 0501798 | 2/1992 | European Pat. Off. |
| 52021332A | 8/1975 | Japan |
| 59-139306 | 1/1983 | Japan |
| 60136501A | 12/1983 | Japan |
| 60142901A | 12/1983 | Japan |
| 61044802A | 8/1984 | Japan |
| 60-061504A | 9/1985 | Japan |
| 05139905A | 8/1993 | Japan |
| 05139906A | 8/1993 | Japan |
| 07076504A | 3/1995 | Japan |
| 2139893A | 11/1984 | United Kingdom |
| 94/12027 | 2/1992 | WIPO |
| 93/25074 | 12/1993 | WIPO |
| 95/17089 | 6/1995 | WIPO |

OTHER PUBLICATIONS

Kelco International Technical Bulletin DB–41–I (1992).
Kelco International Technical Bulletin DB–52–I (1993).
Kelco International Technical Bulletin DB–1.5 (1991).
Kelco International "Alginate Products for Scientific Water Control" (3d Ed., date unknown).

*Primary Examiner*—S. Mark Clardy
*Attorney, Agent, or Firm*—David P. LeCroy

[57] ABSTRACT

A granule suitable for aqueous spray application after tank mix dispersion or dissolution comprises an active ingredient or auxiliary agent, an inert filler and a water-swellable material wherein the water-swellable material is incorporated into the granule in a substantially dry form. Preferred water-swellable materials are non-ionic or predominantly non-ionic and an especially preferred water-swellable material is Xantham gum. The granules provide reduced sludge residues in the spray tank and are particularly well suited for use when housed in a water-soluble bag.

10 Claims, No Drawings

GRANULE COMPOSITION

This invention relates to an improved granule composition and in particular to an improved granule composition having reduced sludge-forming characteristics. The invention is especially applicable to a granule composition suitable for housing in a water-soluble bag.

Active ingredients or auxiliary agents suitable for application by means of an aqueous spray may be formulated in a wide variety of ways. The present invention relates to dry, water-soluble or water-dispersible granule formulations (sometimes also referred to as water-soluble or water-dispersible grain formulations or wettable granules). Such solid granule formulations have a number of advantages as compared with liquid formulations. Such advantages include for example reduced transport costs, reduced operator exposure and reduced residue contamination of containers. A granule formulation may reduce residue formation to the extent that the use of a disposable container is acceptable. Still further reduction in operator exposure and in residue contamination of containers may in some instances be obtained by housing the granules in a water-soluble bag. In particular, contamination following the accidental rupture of a water-soluble bag is greatly reduced if granules are used rather than a liquid formulation within the bag.

A wettable, dispersible or water-soluble granule essentially consists of an agrochemical or other ingredient suitable for application by aqueous spray incorporated with a solid inert filler which may be water-soluble or water-dispersible. The agrochemical or other ingredient may be a solid or liquid and may be water-soluble or water-dispersible. Auxiliary agents such as surfactants, activity enhancers, anti-foams and stabilisers are frequently used and may be incorporated in the same granule with the active ingredient or may be granulated separately or may be added at the tank mix stage.

Such granules may be formed by a variety of techniques, including for example pan granulation, spray drying, agglomeration and extrusion.

In use, the granule is added to water to form a solution or dispersion which is then applied as a spray, for example as a spray application to plants. In agrochemical use for example, the granules are typically mixed immediately prior to spraying with water in a tank containing from about from about 20 liters for a knap-sack sprayer to about 100 to 2000 liters of water for a commercial spray tank. Whilst such tanks are generally provided with some means of agitation, such as mechanical stirring or pumped circulation of the water, the degree of mixing within the tank may be relatively inefficient or the granules themselves may be inherently difficult to disperse, particularly for example if they have been allowed to age. In particular there may be specific zones within the tank ("dead zones") in which the level of agitation is especially poor. In practice therefore effective dispersion of insoluble or partially soluble materials may not be achieved and an insoluble solid sludge may build up in such dead zones within the tank during the time-scale of spray application. Once a sludge is allowed to start to build up, it may become compacted and much harder to re-disperse, even with the application of effective agitation. Even if the sludge is re-dispersed, it may still form relatively large agglomerates of particles which may tend to block the spray nozzles or filters. The formation of sludge in the spray tank is a well-recognised problem which may be associated with the use of granule formulations. Sludge formation can lead to uneven distribution of the active ingredient in the spray and poor biological utilisation of active material.

Sludge left in the spray tank after spraying is completed may cause contamination and disposal problems. One solution to this problem would of course be to provide more efficient agitation within the mixing tank but the cost involved makes this unattractive and a granule formulation which reduces sludge formation in conventional spray tanks is to be preferred.

The problem of sludge formation may actually be exacerbated by the use of a water-soluble bag containing the wettable granule. Typically, the bags will initially float on the surface of the tank whilst they start to dissolve and in the process will tend to accumulate in a surface dead zone caused by the agitation system. As the water-soluble bag continues to dissolve, there is a gradual ingress of water which wets the granules whilst they are still held substantially within the envelope of the dissolving bag. This tends to lead to the agglomeration of particles which may then sink rapidly to a corresponding dead zone at the floor of the tank with correspondingly increased sludge formation.

We have now found that the problem of sludge formation may be reduced by the incorporation into the granule of a water-swellable material which is incorporated into the granule in substantially dry form (that is to say not pre-swelled or wetted).

Thus according to the present invention there is provided a granule suitable for aqueous spray application after tank mix dispersion or dissolution comprising an active ingredient or auxiliary agent, an inert filler and a water-swellable material wherein the water-swellable material is incorporated into the granule in a substantially dry form.

The term "water-swellable material" as used herein includes both materials which swell in the presence of water and subsequently dissolve and materials which swell in the presence of water and subsequently disperse without dissolving.

Preferred water-swellable materials are non-ionic or predominantly non-ionic and include natural and synthetic gums, synthetic polymers and inorganic materials such as water-swellable clays.

It is known to modify the rheology of agrochemical sprays, for example using gelling agents or viscosity modifying agents for a variety of purposes which are completely unrelated to the reduction in sludge formation which is an object of the present invention. Thus for example in U.S. Pat. No. 3,484,229 there is disclosed a sprayable liquid herbicidal composition having reduced spray drift properties which comprises water and a microbial polysaccharide gum. GB 1,395,502 discloses a concentrated thixotropic herbicidal composition comprising an aqueous solution of a salt of a herbicidal bipyridylium quaternary cation containing a gel-forming amount of a gelling agent. The thixotropic composition prevents the herbicide being decanted into unsuitable containers.

It is well known however, and is stressed by the suppliers of materials, that water-swellable materials, and in particular water-swellable gums and polymers must be carefully dispersed in water if they are to be effectively incorporated into the liquid composition without the formation of lumps. Thus, whilst a single granule of a gum will wet immediately when put into water and will then dissolve very rapidly, when a mass of granules is put into water without agitation sufficient for complete dispersion (separation of the individual granules), clumps of granules will be formed. The surfaces of these clumps solvate, forming a layer which prevents wetting of the interior of the clump. Manufacturers recommend for example the use of high-shear mixers to disperse the material.

We have found that, for the very different objective of the present invention, that is to say the reduction of sludge formation resulting from dispersion or dissolution of a solid granular composition, the water-swellable material should be incorporated into the granule in substantially dry form, that is to say without pre-dispersion in water.

When the granule of the present invention is placed in water in the mixing tank, the action of water on the water-swellable material is to cause the whole granule to swell. Although the ultimate objective is to obtain a fully dispersed aqueous composition, we have found that the swelling of the granule actually slows the rapid dispersion of insolubles such as the filler. Contrary to expectation, we have found that this slowing of granule dispersion reduces the tendency of such insolubles to form a sludge in the dead areas of the mixing tank and also tends to reduce any tendency of the dispersed particles to adhere to the walls of the mixing tank. In fact, preferred granules of the present invention swell to form a relatively cohesive swollen mass which we have found retains its cohesion in the absence of agitation or shear, as for example in a dead zone of a mixing tank, but which disperses readily on the application of relatively low shear to provide effective dispersion.

It is an objective of the present invention to reduce sludge formation when such sludge formation is found to be a problem (for example when the granules are housed in a water-soluble bag) and in particular in a tank mixer having an agitation system which results in one or more dead zones of relatively poor agitation and shear. The tendency to sludge formation may be measured by an "Initial Sludge Residue Test" as hereinafter described. Preferred granules of the present invention have a initial sludge residue as herein defined of not greater than 8%, for example not greater than 5%. Granules having an initial sludge residue of not greater than about 2% may be regarded as having excellent sludge properties.

Sludge problems may arise with water-soluble granules when the soluble or partially soluble material is trapped in a zone of poor agitation such that complete dissolution is not achieved. The present invention is however particularly applicable to water-dispersible granules such as granules based on a water-dispersible (insoluble) filler and in particular granules containing a high level of a water-dispersible (insoluble) active ingredient or auxiliary ingredient, since such granules naturally tend to be more prone to sludge formation on tank mixing. Suitably therefore the granule of the present invention has a content of water-insoluble (dispersible) material of at least 10% by weight, for example from 25% to 95% by weight of water insoluble (dispersible) material.

Suitable water-swellable materials include both natural and synthetic gums, synthetic polymers and inorganic materials.

We have found that especially suitable water-swellable materials are non-ionic or predominantly non-ionic materials, since relatively highly charged materials (including for example charged marine gums such as alginates) tend to produce gels by cross-linking with ions in the spray solution, thereby causing additional undesirable gelling and inter-particle agglomeration.

Examples of suitable non-ionic or predominantly non-ionic water-swellable gums and polymers include microbial polysaccharides such as dextran, gellan gum, rhamsan gum and xanthan gum; polysaccharide derivatives such as sodium croscarmellose, microcystalline cellulose, carboxymethyl cellulose, methyl hydroxypropylcellulose, hydroxypropylcellulose, hydroxyethylcellulose, and modified starches; and synthetic polymers such as polyvinyl pyrrolidone, polyvinyl alcohol, cross-linked polyacrylates and poly(methyl vinyl ether/maleic anhydride).

Suitable inorganic materials include water-swellable clays, such as montmorillonite, laponite and bentonite, and aluminium silicate compositions such as veegum..

An especially suitable material is xanthan gum which is readily available, relatively inexpensive and very effective in achieving the objects of the invention.

We have found that the proportion of material to total dry granule ingredients of at least 0.2% by weight and preferably at least 0.5% by weight is suitably incorporated into the granule to achieve the desired swelling and cohesiveness of the granule on addition to water. The term "total dry granule ingredients" includes the dry weight of ingredients used to form the granule but excludes any water added during processing of the granules and excludes any residual water which may remain in the granules once they are formed.

The use of excess material is undesirable, both from a cost point of view and since the presence of excess material may result in the formation of small undissolved globules of water-swellable material which may tend to block filters and spray nozzles. If relatively high levels of water-swellable material are required to overcome a particularly difficult sludge problem, it may be desirable to minimise problems of filter blockage by removing larger particles present in the dry water-swellable material. Thus for example when using a 150 micron nozzle filter in the spray equipment, it may be desirable to sieve the dry water-swellable material to remove any particles of greater than 125 microns.

Thus according to a further aspect of the present invention there is provided a granule formulation suitable for aqueous spray application after tank mix dispersion or dissolution comprising an active ingredient or auxiliary agent, an inert filler and a water-swellable material wherein the proportion of material to total dry granule ingredients is from 0.2% by weight to 8% by weight and preferably from 0.5% by weight to 2% by weight.

We have found that the tendency to sludge formation increases as the temperature of the water into which the granules are dispersed is reduced. This tendency to increased sludge formation may generally be overcome by increasing the proportion of water-swellable material in the granule. Thus a proportion of water-swellable material to total dry granule ingredients of about 1% by weight is especially preferred when the temperature of the water into which the granules are dispersed is about 20° C. whilst the proportion may need to be increased to about 2% or 2.5% by weight if the temperature of the water is only 10° C.

The granule of the present invention may be prepared according to conventional granule techniques, including but not limited to pan granulation, spray drying agglomeration and extrusion. The invention will be illustrated with particular reference to an extrusion granulation technique for which it is particularly well-suited since it is relatively easy in extrusion process to ensure that the water-swellable material spends little time in contact with any process water. In a typical extrusion granulation process the dry ingredients (or the dry ingredients and any liquid active agent or auxiliary agent which may be present) are mixed together in a premix stage. Process water, up to about 40% by weight or more typically up to about 20% by weight is added with mixing to form an extrudable paste. In some instances the active ingredient or one of the auxiliary agents may be added in the form of an aqueous solution or dispersion or may have been produced for example as a damp solid. The process water is then reduced in proportion to the water which has already been incorporated. Low-melting active ingredients or auxiliary agents may if desired be added as a melt.

The extrudable paste is fed to an extruder in which it is forced through dies to form cylindrical particles. After extrusion, the composition is usually dried, for example in a fluidised bed drier. The drying process removes most of the water but the final granule generally contains up to about 5 to 10% of residual water. The resultant granule is typically a cylindrical shaped particle having a diameter in the range from about 0.4 to about 5 mm and a length from about 1 to 10 mm.

In the process of the present invention it is required that the water-swellable material be incorporated into the granule in substantially dry form and more specifically without pre-swelling in water. This is to be contrasted with manufacturers recommendations for the use of water-swellable gums for example which stress that materials should be efficiently dispersed in water, for example using a high-shear mixer, before being used. It is not essential that the material be totally free of water when it is incorporated into the granule, and the material may for example contain water adsorbed from the atmosphere. Similarly, process water will still generally be used in the granulation process. It is desirable however that contact between the process water and the material be minimised in so far as is practicable. Thus for example the substantially dry material may be added last to the premix if any of the ingredients are in the form of an aqueous solution or dispersion (such that the water present in the aqueous solution or dispersion forms all or a part of the process water) and the premixed paste should preferably be granulated and dried relatively soon after the process water has been added.

For example in an extrusion process, the process water is suitably added before or immediately after the water-swellable material and the resultant premix paste is suitably fed to the extruder within one or two hours of preparation and the resultant granules are suitably fed directly to a drier. If the process water is present in the form of an aqueous solution or suspension of one of the other ingredients, the water-swellable material is preferably added to the premixer after the aqueous solution or suspension.

Thus according to further aspect of the present invention there is provided a process for the preparation of a granule suitable for aqueous spray application after tank mix dispersion or dissolution which comprises forming an extrudable paste comprising a water-swellable material which is incorporated as a substantially dry powder, an active ingredient or auxiliary agent, an inert filler and optionally up to 40% by weight of process water, extruding the paste and drying the resultant granule.

Alternatively, the process of the present invention may be used in conjunction with a "dry" extrusion process in which a suitable lubricant is used in place of water.

The water-swellable material may be in the form of a dry, granular or finely divided powder.

The present invention is applicable to any granule suitable for aqueous spray application after tank mix dispersion or dissolution. Thus whilst the present invention is not restricted to any one particular field, such granules are typically used for aqueous sprays in agriculture, public health and animal health.

The active ingredient may for example be a herbicide, insecticide, nematocide, fungicide or plant growth regulator. Alternatively the granule may be used to carry an auxiliary agent such as a wetter or other adjuvant.

Problems of sludge formation are most commonly associated with the use of a water-insoluble filler and dense water-insoluble fillers such as talc may give rise to particular problems by propelling granules rapidly to the floor of the spray tank to form difficult sludges. However, sludge formation may also take place with granules based on water-soluble fillers and the present invention extends to both water-soluble and water-insoluble. Many such fillers are known in the art and a wide commercial choice of filler is available. Examples of typical insoluble fillers include talc, silica, kaolin, pyrophylite, powdered limestone, acid clay, diatomaceous earth, gypsum, pumice, shell powder, mica and silicates. If desired, the water-swellable material, for example a water-swellable clay may also act as filler, but in general it is preferred to use a filler which is not water-swellable.

The granule may contain one or more active ingredients or auxiliary agents and may contain one or more additional components such as a synergist, a humectant, a dye, a pigment, a corrosion inhibitor, a wetting agent or a dispersing agent. It will generally be desirable, but not essential, to include a wetting agent or a dispersing agent in the granule.

Wetting or dispersing agents include cationic, anionic or non-ionic agents. Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, alkyl glucosides, polysaccharides and the lecithins and the condensation products of the said partial esters with ethylene oxide.

The following is a standard method by which the "initial sludge residue" of the granules may be measured and which serves as a definition of this terms. We have found that the initial sludge residue is an excellent measure of the sludge formation which will be found on use of the granule in commercial practice.

DETERMINATION OF "INITIAL SLUDGE RESIDUE"

Apparatus

One dry 600 ml glass beaker of height 140 mm and base diameter 80 mm

One balance accurate to one decimal place

One oven

Procedure

A dry 600 ml glass beaker is weighed (Xg) and about 300 g of water is added. The water will normally be from a sink tap and it is necessary that the temperature of the water is recorded. About 50 g (Z) of granule product is weighed accurately and added to the water. The granules are left in the water for 10 minutes without agitation. The contents of the beaker (including the swollen granules) are poured into an effluent container, after allowing 30 seconds for drainage of the residue from the upturned vessel. The beaker is then transferred to an oven at 50° C. in order to dry the wet residue. After 30 minutes (or when the residue is dry) the mass of the glass beaker plus residue (W) is determined.

The initial sludge residue (%) is then quoted as $$\frac{(W - X)}{Z} \times 100$$

The invention is illustrated by the following Examples in which all parts and percentages are by weight unless otherwise stated. The percentage by weight of components present in a granule are expressed in terms of the total dry weight of the components of the granule, ignoring any residual process water which may be present in the granule following drying.

It will be appreciated that the initial sludge residue is an important measure of the cohesiveness of a swollen granule, since a cohesive granule will retain its integrity under the low-shear conditions of the test and will not therefore produce significant quantities of sludge. Preferred water-swellable materials are such that a Standard Granule, prepared as in Example 7, has an initial sludge residue as herein defined of less than 8%.

EXAMPLE 1

Granules were prepared by extrusion of a wet paste using the following general method applicable to a 500 g scale: All dry ingredients except the water-swellable material were mixed for two minutes and the active agrochemical was then added (dropwise for a liquid) followed by the required weight of water-swellable material. Mixing was continued in a blender for a further two minutes and sufficient process water to give an extrudable paste (approximately 100 ml) was added over about 30 seconds. Mixing was continued for about 1 minute and the resultant paste was transferred to a laboratory scale extruder equipped with a 1 mm screen. The paste was extruded and the resultant granules were dried for 10 to 15 minutes in a fluid bed drier at 50° C. The product was sieved to remove oversize and undersize granules.

A series of granules were prepared using the components listed below and varying proportions of water-swellable material as indicated in Tables 1 and 2.

Granule A

| Component | Proportion by weight (based on total dry weight) |
|---|---|
| lambda-cyhalothrin | 2.5% |
| KELZAN | See Table 1 |
| Wetter/dispersant | 15.0% |
| Filler (talc/aluminium silicate) to | 100% |

KELZAN (trademark of Monsanto) is an industrial grade xanthan gum supplied as a free-flowing powder/granules of 28 mesh size.
Lambda-cyhalothrin is a pyrethroid insecticide.
Granule B

| Component | Proportion by weight (based on total dry weight) |
|---|---|
| Pirimicarb | 17.5% |
| KELZAN | See Table 1 |
| Wetter/dispersant | 12.5% |
| Filler (sodium acetate/talc) to | 100% |

Pirimicarb is a dimethylcarbamate insecticide.

TABLE 1

Granule A (Lambda-Cyhalothrin)

| KELZAN content (% by weight) | Initial sludge residue (%) |
|---|---|
| 4.8 | 3.75 |
| 2.4 | 5.15 |
| 1.0 | 3.80 |
| 0.8 | 3.40 |
| 0.5 | 4.22 |
| 0.2 | 3.91 |
| 0 | 8.08 |

TABLE 2

Granule B (Pirimicarb)

| KELZAN content (% by weight) | Initial sludge residue (%) |
|---|---|
| 4.8 | 1.16 |
| 2.4 | 1.17 |
| 1.0 | 2.39 |
| 0.8 | 1.61 |
| 0.5 | 3.50 |
| 0.2 | 4.95 |
| 0 | 4.41 |

EXAMPLE 2

The procedure of Example 1 was repeated using a granule formulation containing 5% lambda-cyhalothrin rather than 2.5%. The results are presented in Table 3.

TABLE 3

| KELZAN content (% by weight) | Initial sludge residue (%) |
|---|---|
| 4.8 | 1.5 |
| 2.4 | 3.7 |
| 1.0 | 3.0 |
| 0.8 | 3.8 |
| 0.5 | 3.6 |
| 0.2 | 4.4 |
| 0 | 7.6 |

EXAMPLE 3

Granules containing 2.5% by weight lambda-cyhalothrin and 1% by weight KELZAN were prepared using the general method of Example 1 except that the extruder screen was 0.6 mm and that (according to a less preferred option) the KELZAN was added before the liquid lambda-cyhalothrin. Comparison granules containing no KELZAN were prepared using the same method.

The granules were sealed within 12 water-soluble bags (formed from M7030 polyvinyl alcohol film (38 $\mu$m thick) supplied by Chris-Craft Industrial Products Inc.) each containing 50 g of granules. Spray solutions were prepared in a Horstine Farmery tank mix rig which was filled to 250 liter with water at 15° C., agitated at 100 liter per minute. The granule-containing bags were added and the water-soluble bag was allowed to rupture under the action of the water in the tank. The solution was the sprayed one minute after bag rupture.

The granules according to the invention produced 9% sludge (calculated gravimetrically allowing for solubles) whilst the comparison granules not containing KELZAN produced 21% sludge calculated in the same way.

EXAMPLE 4

The procedure of Example 3 was followed (using the same proportions of reactants) except that the liquid lambda-cyhalothrin was added before the KELZAN and the temperature was 22 to 24° C. A different but essentially equivalent grade of polyvinyl alcohol film (M8030) was used to manufacture the water-soluble bags. The granules according to the invention produced 1% sludge (calculated gravimetrically allowing for solubles) whilst the comparison granules containing no KELZAN produced 27% sludge calculated in the same way.

EXAMPLE 5

The procedure of Example 1 was used to prepare granules containing 2.5% by weight of lambda-cyhalothrin and 1% by weight of a variety of water-swellable materials according to the invention. The granules were sealed within 12 water-soluble bags (formed from either M7030 polyvinylalcohol film or M8030 polyvinylalcohol film supplied by Chris-Craft Industrial Products Inc.) each containing 50 g of granules. Spray solutions were prepared using the procedure of Example 3 and the sludge levels remaining after spraying were measured gravimetrically as in Example 3. The temperature of the spray tank was between 18° C. and 24° C. The results are presented in Table 4:

TABLE 4

| Water-Swellable Material | Description | Sludge Level (%) |
| --- | --- | --- |
| KELZAN | Xantham gum supplied by Kelco | 1 |
| LAPONITE RD | Water-swellable clay supplied by Laporte Industries | 21 |
| Bentonite STP300s | Water-swellable clay supplied by Wilfrid Smith Ltd. | 16 |
| PVP K-90 (AGRIMER 90) | Polyvinylpyrollidone | 5 |
| Rhamsan gum | rhamsam gum | 7 |
| Control (No water-swellable Material) | | 27 |

EXAMPLE 6

The procedure of Example 1 was followed to produce granules containing 5.0% by weight of lambda-cyhalothrin (in place of the 2.5% used in Example 1) and either 1.0% KELZAN or 2.5% KELZAN. The material used for the water-soluble bag was a mixture of M7030 and M 8030 polyvinylalcohol film. Spray solutions were produced as in Example 3 and the sludge levels remaining after spraying were determined gravimetrically. The results are as indicated in Table 5:

TABLE 5

| Proportion of KELZAN (%) | Water Temperature (° C.) | Sludge Level (%) |
| --- | --- | --- |
| 2.5 | 10 | 0 |
| 1 | 23 | 9 |
| 1 | 11 | 21 |
| 0 | 24 | 30 |
| 0 | 11 | 24 |

Some undesirable build-up of material on the filter nozzles was observed during spraying when using granules containing 2.5% KELZAN.

EXAMPLE 7

The procedure of Example 1 was repeated to prepare "Standard Granules" incorporating a range of water-swellable materials whose "Initial Sludge Residue" was then determined according to the standard method. No water-soluble bag was used.

The composition of the Standard Granule was as follows:

| | Content (% by weight) |
| --- | --- |
| Wetter/dispersant | 15 |
| Water-swellabe material (Table 6) | 1 |
| Filler (Talc/Aluminium silicate) To | 100% |

The Initial Sludge Residue Values for various water-swellable materials incorporated in a Standard Granule are given in Table 6.

TABLE 6

| Water-Swellable Material | Description | "Initial Sludge Residue" |
| --- | --- | --- |
| KELZAN (supplied by Kelco) | Xantham Gum | 4.2 |
| RHEOZAN (supplied by Rhone Poulenc) | Xantham Gum | 7.4 |
| RHODOPOL (supplied by Rhone Poulenc) | Xantham Gum | 1.4 |
| RHAMSAN GUM K1A112 (supplied by Kelco) | Rhamsan Gum | 6.3 |
| AGRIMER 90 PVP K -90 (supplied by GAF) | Polyvinylpyrrolidone | 4.8 |
| BENTONITE STP 300S (supplied by Wilfred Smith Ltd) | Clay | 5.9 |
| LAPONITE RD (supplied by Laporte Absorbants) | Clay | 6.6 |
| COURGEL AG5000 (supplied by Courtaulds Fine Chemicals) | Hydroxypropylmethyl Cellulose | 6.3 |
| CARAGEENAN GUM TPC-1 (supplied by Hercules) | Carageenan Gum | 4.6 |

EXAMPLE 8

This Example illustrates the formation of a water-soluble granule containing a relatively high loading of fluazifop-p-butyl and having reduced sludge properties when used without a water-soluble bag housing.

The compositions were as follows:

COMPOSITION 8.1 (Control containing no water-swellable material)

| INGREDIENT | CONTENT (% BY WEIGHT) |
| --- | --- |
| fluazifop-p-butyl | 50 |
| BRIJ 96 (non-ionic ethoxylate) | 3 |
| SOPROPHOR 4D384 (Ttristrylphenol ethoxylate) | 4 |
| TAMOL PP (phenolic formaldehyde condensate) | 8 |
| GEROPON T36 (polycarboxylate dispersant) | 3 |
| CARFLO E (calcium silicate filler) to | 100% |

COMPOSITION 8.2

| INGREDIENT | CONTENT (% BY WEIGHT) |
|---|---|
| fluazifop-p-butyl | 50 |
| BRIJ 96 (non-ionic ethoxylate) | 3 |
| SOPROPHOR 4D384 (Ttristrylphenol ethoxylate) | 4 |
| TAMOL PP (phenolic formaldehyde condensate) | 8 |
| GEROPON T36 (polycarboxylate dispersant) | 3 |
| AGRIMER AL10 * | 1 |
| CARFLO E (calcium silicate filler) to | 100% |

* AGRIMER AL10 is a polyvinylpyrollidone with 10% butylation on various positions within the copolymer.

COMPOSITION 8.3

| INGREDIENT | CONTENT (% BY WEIGHT) |
|---|---|
| fluazifop-p-butyl | 50 |
| BRIJ 96 (non-ionic ethoxylate) | 3 |
| SOPROPHOR 4D384 (Ttristrylphenol ethoxylate) | 4 |
| TAMOL PP (phenolic formaldehyde condensate) | 8 |
| GEROPON T36 (polycarboxylate dispersant) | 3 |
| KELZAN | 1 |
| CARFLO E (calcium silicate filler) to | 100% |

Granules based on Composition 8.1 were prepared as follows: Fluzifop-p-butyl, BRIJ 96 and SOPROPHOR 4D384 were mixed to form a pre-cursor emulsion concentrate. CARFLO E, TAMOL PP and GEREPON T36 were then charged into a mixing vessel and well mixed. The emulsion concentrate was added slowly to the powder mixture and process water (approximately 10 parts per hundred by weight) was added with mixing until the blend reached a consistency suitable for extrusion. The blend was extruded and the resultant granules dried at 50° C. for 20 minutes. Granules based on Composition 8.2 were similarly prepared except that the AGRIMER AL10 was added to the process water. Granules based on Composition 8.3 were similarly prepared except that the KELZAN was added to the blend in dry powder form followed by the process water.

Spray solutions were prepared and sprayed using a Horstine Farmery sprayer as in Example 3. The temperature of the water in which the granules were dispersed was between 16 and 18° C.

The granules according to the invention containing 1% by weight KELZAN produced no measurable sludge whilst those containing 1% by weight of AGRIMER AL10 produced 15% sludge (calculated gravimetrically allowing for solubles). The comparison granules containing no water-swellable material produced more than 30% sludge calculated in the same way.

What is claimed is:

1. A process for the preparation of a granule suitable for aqueous spray application after tank mix dispersion or dissolution which comprises (i) forming an extrudable paste comprising a water-swellable material which is a microbial polysaccharide or a polysaccharide derivative which is incorporated as a substantially dry powder, an active ingredient or auxiliary agent, an inert filler and, optionally, up to 40% by weight of process water, (ii) extruding the paste, and (iii) drying the resultant granule.

2. A process according to claim 1 wherein the process water is added to the extrudable paste either before the substantially dry water-swellable material has been incorporated or immediately after the water-swellable material has been incorporated and the resultant extrudable paste is fed to the extruder within one hour of preparation and the extruded granules are then fed directly to a drier.

3. A granule having reduced sludge-forming characteristics suitable for aqueous spray application after tank mix dispersion or dissolution comprising an active ingredient or auxiliary agent, an inert filler and a water-swellable material which is a microbial polysaccharide or a polysaccharide derivative wherein the water-swellable material is incorporated into the granule in a substantially dry form.

4. A granule according to claim 3 wherein the water-swellable material is a xanthan gum.

5. A granule according to claim 3 wherein the proportion of water-swellable material to total dry granule ingredients is from 0.2% by weight to 8% by weight.

6. A granule according to claim 5 wherein the proportion of water-swellable material to total dry granule ingredients is from 0.5% by weight to 2% by weight.

7. A granule according to claim 3 wherein the active ingredient is a herbicide, insecticide, nematocide, fungicide or plant growth regulator.

8. A granule according to claim 3 which additionally contains one or more additional components selected from a synergist, a humectant, a dye, a pigment, a corrosion inhibitor, a wetting agent or a dispersing agent.

9. A granule according to claim 3 wherein the inert filler is not water-swellable and is water-insoluble.

10. A granule according to claim 3 wherein the water-swellable material is such that a Standard Granule as herein defined has an initial sludge residue as herein defined of less than 8%.

* * * * *